United States Patent [19]

Pebley et al.

[11] Patent Number: 5,298,261
[45] Date of Patent: Mar. 29, 1994

[54] RAPIDLY DISINTEGRATING TABLET

[75] Inventors: Walter S. Pebley; Norman E. Jager; Sally J. Thompson, all of Albany, Oreg.

[73] Assignee: Oregon Freeze Dry, Inc., Albany, Oreg.

[21] Appl. No.: 995,196

[22] Filed: Dec. 24, 1992

Related U.S. Application Data

[62] Division of Ser. No. 871,556, Apr. 20, 1992.

[51] Int. Cl.$^5$ ................................................ A61K 9/20
[52] U.S. Cl. .................................... 424/488; 424/464; 424/484; 424/485
[58] Field of Search ............... 424/464, 469, 484, 485, 424/488

[56] References Cited

U.S. PATENT DOCUMENTS

| | | | |
|---|---|---|---|
| Re. 33,086 | 10/1989 | Bru | 424/44 |
| 4,001,944 | 1/1977 | Williams | 34/5 |
| 4,305,502 | 12/1981 | Gregory et al. | 206/532 |
| 4,347,671 | 9/1982 | Dias et al. | 34/15 |
| 4,371,516 | 2/1983 | Gregory | 424/485 |
| 4,470,962 | 9/1984 | Keith et al. | 424/486 |
| 4,616,047 | 10/1986 | Lafon | 523/105 |
| 4,704,268 | 11/1987 | Kifune | 424/488 |
| 4,713,249 | 12/1987 | Schroder | 424/484 |
| 4,758,598 | 7/1988 | Gregory | 424/484 |
| 4,832,956 | 5/1989 | Gergely et al. | 424/480 |
| 4,946,684 | 8/1990 | Blank et al. | 424/485 |
| 5,008,114 | 4/1991 | Lovrecich | 424/464 |
| 5,047,248 | 9/1991 | Calanchi et al. | 424/485 |
| 5,079,018 | 1/1992 | Ecanow | 426/385 |
| 5,082,655 | 1/1992 | Snipes et al. | 424/484 |
| 5,128,143 | 7/1992 | Baichwal et al. | 424/458 |
| 5,132,116 | 7/1992 | Sournac et al. | 424/464 |

FOREIGN PATENT DOCUMENTS

895546 7/1989 South Africa .
2111423A 7/1983 United Kingdom .

*Primary Examiner*—Thurman K. Page
*Assistant Examiner*—Amy Hulina
*Attorney, Agent, or Firm*—Klarquist Sparkman Campbell Leigh & Whinston

[57] ABSTRACT

A tablet that rapidly disintegrates in aqueous solution includes a partially collapsed matrix network that has been vacuum-dried above the collapse temperature of the matrix. The matrix is preferably at least partially dried below the equilibrium freezing point of the matrix. Vacuum drying the tablet above its collapse temperature instead of freeze drying it below its collapse temperature provides a process for producing tablets with enhanced structural integrity, while rapidly disintegrating in normal amounts of saliva. The tablet preferably carries a drug, such as acetaminophen. The matrix network of the tablet preferably includes a gum, a carbohydrate and the drug. Especially preferred embodiments also include a flavoring, a sweetener and surfactant. The gum is preferably acacia, guar, xanthan, carrageenan or tragacanth gum. The carbohydrate is preferably mannitol, dextrose, sucrose, lactose, maltose, maltodextrin or corn syrup solids.

9 Claims, 5 Drawing Sheets

RAPIDLY DISINTEGRATING TABLET

This is a division of application Ser. No. 07/871,556, filed Apr. 20, 1992, pending.

BACKGROUND OF THE INVENTION

1. Field of the Invention

This invention concerns pharmaceutical delivery forms, more particularly tablets for oral administration that disintegrate in an aqueous solution, such as saliva. The tablets disintegrate rapidly in the saliva of a subject's mouth, and can be swallowed easily without drinking water.

2. General Description of the Background

Lyophilization (which is also known as freeze-drying) is a technique for removing moisture from a wet material by freezing it and subsequently subliming moisture from it under reduced pressure. In this process, a suspension, solution or wet solid is frozen, and ice crystals in the frozen product are removed through a sublimation process at a reduced temperature and pressure that transforms ice directly into a vapor. The resulting freeze-dried product is a porous mass about the same size and shape as the original frozen mass. It has good stability, convenient reconstitutability when placed in solvent (usually water), and maintains flavor and texture similar to the original material.

Typical freeze-drying operations require three steps: freezing, removal of unbound liquid (primary drying) by sublimation from a solid directly into a vapor, and desorption of bound solvent (secondary drying) from a liquid into a vapor. Materials to be freeze-dried may be complex mixtures of solvent(s) and other substances that are cooled to form ice crystals. With further cooling, the mass becomes more rigid as the result of formation of eutectics. When the entire mass is solidified, all unbound solvent has been transformed into ice. Bound solvent, however, remains fixed as a liquid within the internal structure of the material and is not frozen.

During the sublimation phase of freeze-drying, the frozen material is exposed to a vacuum, and heat is applied to the ice crystals to sublime them. The temperature and pressure of the lyophilization process is carefully controlled such that the frozen mass is maintained below the eutectic temperature at which the mass begins to melt. Maintaining the temperature of the treated mass lower than its eutectic temperature is considered critical to providing a freeze-dried product. See, for example, U.S. Pat. No. 4,616,047 and U.S. Pat. No. 4,001,944, which stress that lyophilization occurs below the initial melting temperature of the mass. Removing unbound solvent during the primary drying step is therefore accomplished without exceeding the eutectic temperature of the composition. Direct sublimation from a solid to a vapor has been considered important to forming the microporous structure that gives freeze-dried products their porosity and reconstitutability.

Lyophilization processes have been used to prepare tablets that are described as rapidly dissolving in a subject's mouth. Such tablets are shown in U.S. Pat. Nos. 4,371,516 and 4,946,684, as well as GB 2,111,423 and South African Patent Application No. 895546. These patents disclose pharmaceutical tablets having an open matrix network structure containing gelatin or a natural gum and a carbohydrate such as mannitol. U.S. Pat. No. 4,946,684, for example, describes tablets containing mannitol and gum that are prepared by a lyophilization process in which the tablet is initially frozen. Moisture is then sublimed from the tablet below the initial melting temperature of the mixture. Direct sublimation of liquid from the tablet has been found to produce a very porous open matrix network throughout the tablet into which saliva rapidly moves to disintegrate the lyophilized mass after it is placed in a subject's mouth.

Although the open matrix network of these lyophilized products produces a tablet that rapidly disintegrates in water or saliva, a drawback is that such tablets are very fragile, and their handling prior to placing in the mouth must be severely restricted. U.S. Pat. No. 4,305,502 attempts to overcome the problem of the freeze-dried tablet's fragility by forming and lyophilizing the tablets in the depressions of a plastic blister package. The depressions are then covered by an adherent sheet to seal the package and protect the tablets during storage.

The fragile nature of freeze-dried products has often impeded their more widespread use. Until now it has been thought that loss of tablet integrity was a necessary sacrifice to obtain a tablet that dissolved readily in the mouth.

Vacuum drying is an alternative method of removing liquid from a material by evaporating the liquid at a reduced pressure. Although vacuum drying is widely used in laboratory and industrial applications, it suffers from the drawback of producing explosive release of liquid from the material being dried. This explosive release disrupts the structure of the material, and has heretofore been considered unsuitable for commercial production of well formed or shaped products.

It is an object of the present invention to provide a process for producing improved rapidly disintegrating tablets that have enhanced structural integrity.

It is yet another object of the invention to provide an improved rapidly disintegrating tablet that can be dislodged from a blister pack with minimal damage to the tablet.

It is yet another object of the invention to provide such an improved tablet that has a taste and texture acceptable to consumers.

These and other objects of the invention will be understood more clearly by reference to the following detailed description and drawings.

SUMMARY OF THE INVENTION

The foregoing objects have been achieved in the present invention by disregarding prior tablet lyophilization processes in which solid unbound moisture is directly sublimed from a solid to a gas. The present inventors have instead prepared a rapidly disintegrating tablet by vacuum drying unbound liquid from a tablet matrix above the collapse temperature, where the collapse temperature is the initial melting point or eutectic temperature of the matrix. Vacuum drying above the collapse temperature during primary drying allows evaporation of free unbound solvent (such as water) to occur from a solid through the liquid phase to a gas under controlled conditions, instead of subliming from a solid directly to a gas as in lyophilization. When the matrix reaches its collapse point, the structure of the matrix partially collapses and becomes more dense. The resulting vacuum dried tablet, as compared to a lyophilized tablet, has lower porosity, greater density, and is less likely to be broken by mechanical forces exerted on the tablet.

Vacuum drying preferably is performed throughout the primary drying stage at a temperature below the equilibrium freezing point of the composition, at which point the solvent (such as water) in the mixture changes phase. As the primary drying temperature reaches the equilibrium melting point in a reduced pressure environment, local areas of structural disruption can occur due to eruption of liberated liquid from the melting matrix. This problem is diminished by maintaining the temperature of the matrix during primary drying between the collapse temperature and the equilibrium freezing point.

Vacuum drying uses subatmospheric pressure conditions to enhance removal of unbound solvent from the matrix during primary drying. Although any subatmospheric pressure will achieve this result, the present inventors have also found that it is preferable (although not required) to retard the phase change that occurs at the collapse point by selecting a suitable vacuum pressure, for example 0.5 to 10 torr. Such low pressures retard the rate of phase change occurring at the collapse temperature. Vacuum drying closer to atmospheric pressure (760 torr) results in a more rapid and complete phase change at the collapse temperature. The more controlled and slower phase change at low pressure is preferred because it produces a tablet having particularly good structural integrity. Hence, low pressures (e.g., 0.5-10 torr) are preferred in the vacuum drying chamber, particularly if the primary drying temperature is near the collapse temperature (e.g. 1°-5° C. above the collapse temperature). As the primary drying temperature approaches the equilibrium freezing point of the mass, local disruptions of the matrix may occur at higher pressures (for example higher than 10 torr) as local areas of solvent melt and the liquid is rapidly evolved from the tablet. Hence a lower pressure (for example 2.0 torr) is preferred as the temperature approaches the equilibrium freezing point (for example, from about 5° C. below the equilibrium freezing point).

The tablet is a pharmaceutical dosage form suitable for oral administration as a solid that rapidly disintegrates in aqueous solution. The product has a partially collapsed matrix network containing a pharmacologically acceptable carrier material. The matrix has preferably been vacuum dried during primary drying above the collapse temperature of the matrix. The matrix preferably includes a pharmaceutical compound which can be delivered and taste masked by the dissolving matrix. In preferred embodiments, the matrix contains a pharmaceutically effective amount of the active ingredient, 0.1-3.0% of a gum, and 10-60% of a carbohydrate base. All percentage weights throughout the specification and claims are dry weight when referring to a vacuum dried tablet (as here), and wet weight when referring to a formulation from which a tablet is made (as in Formulations 1-81). The gum is preferably selected from the group consisting of acacia, guar, xanthan, carrageenan, and tragacanth gum. The carbohydrate is preferably mannitol, dextrose, sucrose, lactose, maltose, maltodextrin, corn syrup solids, or mixtures thereof.

The active ingredient may be a particulate powder or crystalline material encapsulated as necessary, with a taste masking material such as partially hydrogenated cottonseed oil, corn oil, cellulose, flavored oil, zein, candied sugar, other encapsulating materials, or mixtures thereof. Many other pharmaceutical agents can be used in the tablet, including (without limitation) ibuprofen, caffeine, benzodiazepines, dextromethorphan cough suppressants, and veterinary medications. The tablet may also contain a flavor enhancer that further masks the taste of the drug, and a surfactant for enhancing dispersion of the ingredients and preventing adhesion of the tablet to the receptacle in which the tablet is formed.

In some preferred embodiments, the tablet comprises (by dry weight) an active ingredient in the amount of 1-60%, preferably 10-60% (without encapsulation), a carbohydrate base in an amount of 10-60%, a gum in an amount of 0.1-3.0%, 0.001-5.0% flavoring less than 1% surfactant and less than about 1% sweetener. In particularly preferred embodiments, the tablet comprises 30-45% acetaminophen powder (not including the weight of any encapsulation), 20-45% carbohydrate, and 0.1-0.5% (preferably 0.4%) gum. In other preferred embodiments, the tablet comprises 35% acetaminophen powder as the active ingredient, 40% mannitol, 0.4% xanthan gum, 0.3% mono-ammonium glycyrrihizinate sweetener, 0.15% aspartame, 1% wintergreen flavoring, and 0.01% nonionic surfactant. The tablets are preferably made from a formulation that is 25-35% w/w distilled water.

The present invention also includes a method of preparing a pharmaceutical tablet that can be orally administered and that disintegrates in an aqueous liquid solvent, such as saliva. The method includes the steps of preparing a mixture that includes sufficient amounts of water, gum and a carbohydrate to form a rapidly dissolving tablet. The mixture is formed into a desired tablet shape, frozen below its collapse point to form a solid matrix, and vacuum dried during primary drying above the collapse temperature, and preferably below the equilibrium freezing temperature of the mixture, to form the tablet. The tablet has a partially collapsed matrix that exhibits a higher density than freeze dried products, reduces fragility of the tablet, and may prolong disintegration time. The shaped solid dosage form preferably contains a pharmaceutically active material that is distributed (preferably uniformly) throughout the dosage form.

The dosage form of the present invention preferably disintegrates in the mouth of a human or veterinary subject in twenty to sixty seconds.

DETAILED DESCRIPTION OF A PREFERRED EMBODIMENT

The pharmaceutical product of the present invention is a tablet that disintegrates rapidly in the mouth, provides adequate dosage levels of a drug, masks the taste of an active ingredient, and has sufficient structural integrity to withstand handling without substantial breakage of the tablet. These advantages are achieved by forming a mixture (such as a slurry or paste) into a desired shape, freezing the mixture at a temperature that forms a solid matrix, then vacuum drying the matrix above its collapse temperature but below its equilibrium freezing temperature to form a partially collapsed matrix network. The mixture contains sufficient amounts of a gum, water and carbohydrate (as illustrated in the following examples) to form the solid frozen matrix that is then vacuum dried to form the tablet. The matrix network is sufficiently porous to allow liquid (such as saliva in the oral cavity) to enter the pores of the tablet and cause rapid disintegration of the tablet.

Vacuum drying the matrix under the conditions described above allows the matrix to be relatively or partially collapsed in comparison to the structure of the same matrix had it been lyophilized. Vacuum drying the mixture above its collapse temperature allows solvent in the mixture to evaporate from a solid through the liquid phase to a gas. This vacuum drying of moisture through a liquid phase, as opposed to sublimation of water by freeze drying from a solid phase, results in a partially collapsed matrix that has greater density and is less fragile than freeze-dried tablets. The vacuum dried matrix has an increased mobility above the collapse temperature (as dissolved carbohydrate starts to fuse with other particles of carbohydrate and increasingly mobile solvent) to allow liquefaction to occur and permit evaporative primary drying of unbound water. The partially collapsed matrix of the present invention contrasts with the open matrix of lyophilized tablets in which direct sublimation of solvent leaves large pores. It is the open pore structure of the lyophilized matrix that makes such tablets more fragile and less dense than the partially collapsed matrix tablets of the present invention.

The tablets preferably contain an active ingredient, such as encapsulated acetaminophen, preferably (by dry weight) in a range of 1-60%, more preferably 10-60%. (These ranges do not include the weight of the encapsulating material). Although a lower percentage of acetaminophen ingredient can be used, a very low percentage may require an unacceptably large tablet to achieve a sufficiently therapeutic dosage of the drug. A percentage of drug higher than the preferred range can produce a product that is more difficult to pump as a liquid, and a tablet that has unacceptably slow disintegration in aqueous solution. Very potent drugs can be present in small amounts, such as 10%, without making the tablet unacceptably large. When the active ingredient has a bitter taste, such as acetaminophen, that ingredient is preferably encapsulated with a material such as partially hydrogenated cottonseed oil, corn oil, flavored oil, zein (corn protein), cellulose and candied sugar. Encapsulation with one or more of these materials has been found to enhance the palatability of acetaminophen while the tablet is dissolving in the mouth.

The tablet also includes a carbohydrate base, such as mannitol, which provides structural integrity when the tablet is dry, and rapid disintegration in the presence of a liquid such as saliva. The carbohydrate base is preferably present in an amount of 10-60% dry weight. A lower percentage of carbohydrate base can reduce the structural integrity of the tablet and result in unsatisfactory organoleptic qualities. A percentage of carbohydrate above the preferred range produces a tablet that is large, denser, and dissolves more slowly. Some of the carbohydrates that have been found suitable for use in the present invention include dextrose, sucrose, lactose, maltose, maltodextrin, corn syrup solids, and combinations of sucrose/dextrose, corn syrup solids/mannitol, dextrose/mannitol, and maltodextrin/mannitol. However, the preferred carbohydrate is mannitol because it vacuum dries well, is not hygroscopic, and has a cool mouth feel due to its negative heat of solution.

A gum is used as a thickener in the mixture of the present invention. It serves to maintain the active ingredient in homogenous suspension and thereby achieve uniform distribution throughout the mixture. The gum also contributes to formation of the matrix, and provides a more palatable mouth feel of the tablet before and during disintegration. The gum is preferably present in the dry weight range of 0.1-3.0%. At least 0.1% of the preferred xanthan gum is preferred to keep the active ingredient in suspension. Xanthan and carrageenan gums have been found to be quite suitable for this purpose, although other gums that can be used include acacia, guar, and tragacanth gum. A maximum amount of 3.0% of gum is desirable to provide a tablet having a suitable mouth feel.

Especially preferred embodiments include a surfactant in the formulation to improve the flow qualities of the wet mixture and act as an emulsifier to prevent oil and water separation. A preferred surfactant has been found to be polysorbate 60, in an amount of 1.0% dry weight or less. Greater amounts of surfactant may produce an unpleasant taste. Successful embodiments of the present invention have been made without a surfactant.

Another optional ingredient of the present invention is a flavoring (for example, cherry or wintergreen). Flavorings may be used to provide an acceptable sensory appeal and mask bitterness. The flavorings are preferably used in an amount of 0.001-5.0% dry weight, but fruit powders, concentrates or purees can be used in higher amounts. In preferred embodiments, flavoring is any suitable natural, artificial or combined natural and artificial flavoring or flavor enhancer, such as maltol, ethyl maltol, citric acid, ascorbic acid or acetaldehyde.

Sweeteners are optionally used in the tablet to provide an acceptable sensory appeal and mask bitterness of an active ingredient. The range of amounts of sweeteners used varies substantially depending upon the identity of the sweetener. Artificial sweeteners are preferred because their potency allows a minimal amount of the sweetener to be present in the tablet. Some sweeteners that have been used in tablets of the present invention include acesulfame-K (SUNETTE), aspartame, sodium saccharin, calcium saccharin, and mono-ammonium glycyrrihizinate (MAGNASWEET or MAG). Mono-ammonium glycyrrihizinate and aspartame are used as sweeteners in preferred embodiments of the invention described below. A desirable amount of the particular sweetener to be used can easily be determined The tablet of the present invention may be made without a sweetener, because the sweetener is not important to formation of the drug carrying matrix Unsweetened tablets are, however, less palatable.

The present invention will be better understood by reference to the following specific examples.

EXAMPLE I

A preferred embodiment of the rapidly disintegrating tablet of the present invention contains the following ingredients, designated formulation 1, with the respective amounts listed by wet weight.

| Formulation 1 | |
|---|---|
| INGREDIENT | PERCENT |
| ENCAPSULATED ACETAMINOPHEN | 35.00 |
| MANNITOL | 30.00 |
| XANTHAN GUM | 0.30 |
| MONO-AMMONIUM GLYCYRRIHIZINATE | 0.30 |
| ASPARTAME | 0.15 |
| WINTERGREEN FLAVOR | 1.00 |
| POLYSORBATE 60 | 0.01 |
| DISTILLED WATER | 33.24 |

The encapsulated acetaminophen was Durkote APAP 145-75 obtained from Van Den Bergh Food Ingredients Group of Lisle, Ill. The gum was Kelco Xanthan Gum K1B111. The flavoring was DM Wintergreen 1348.

The tablet formulation was made in a HOBART mixing bowl in which the required amount of water was placed at room temperature (24° C.), and the mixer was turned on. The polysorbate was preheated to a flowable liquid (30° C.), and the required amount of liquid polysorbate was added to the water and mixed for 30-60 seconds. The Wintergreen flavor powder was then slowly added to the mixing solution until all lumps were dissolved. The aspartame and mono-ammonium glycyrrihizinate were next added to the mixing solution until all lumps were dissolved. Xanthan gum was then added and mixed in thoroughly, followed by mannitol, which was added to the solution and mixed until all lumps were dissolved. Finally, the encapsulated powdered acetaminophen was added to the mixing solution until all lumps were dissolved and a slurry mixture was formed. The mixer was then turned off, and the slurry from the mixing bowl was transferred into an intake tube. A 1.2 g amount of the mixture was deposited from the tube into one of the pre-formed indentations in a plastic blister pack to achieve a 325 mg acetaminophen dosage. The blister pack was obtained from Rexham Packaging of Orange, Conn., under product designation number 1025.

The plastic blister pack was placed in a cold room at −40° C. for 8 hours such that the mixture formed a frozen matrix in the indentation. Vacuum drying was then performed in an Edwards Lyoflex 1.8 vacuum dryer by pre-chilling the shelves of the vacuum dryer to −20° C. The blister pack containing the frozen tablets was then placed on shelves, the dryer door was closed and a vacuum was pulled to about 2.000 mbar, which was maintained for 15 minutes to allow equilibration between the temperature of the frozen mixture and the dryer. Shelf temperature was then increased rapidly to +35° C. Shelf temperature and vacuum level was maintained at these levels for 4.0 hours to vacuum dry the product at above the collapse temperature. The chamber was then purged with nitrogen gas to bring it to atmospheric pressure, and the blister pack was removed from the dryer.

EXAMPLE II

The same formulation was used as in Example I, except the amount of mannitol was lowered to 23%. The tablets in the blister pack were frozen at −40° C. for 8 hours to form a solid matrix, but the shelves of the vacuum dryer were pre-chilled to −47° C. The blister pack containing the frozen mixture was then placed on shelves, the dryer door was closed and the vacuum was pulled to less than 0.550 mbar, which was maintained for 15 minutes to allow equilibration between the temperature of the frozen mixture and the dryer. Shelf temperature was then increased rapidly to +35° C., and once the shelf temperature reached +35° C. for 15 minutes, the vacuum was decreased to 2.000 mbar. Shelf temperature and vacuum level was maintained at these levels for 4.0 hours to vacuum dry the product at above the collapse temperature. The chamber was then purged with nitrogen as in Example I above.

EXAMPLE III

The tablet of the present invention can be formed by many different methods. The mixture can, for example, be placed in indentations on a freezing belt, drum or other device to form the tablet. Once the tablets are solidified, they may be removed and placed in bulk on a tray inside the vacuum dryer.

EXAMPLE IV

Determining Collapse Temperature With DSC

The collapse temperature of the frozen mixture was determined by differential scanning calorimetry (DSC). The thermograms were obtained with a DuPont 2000 DSC from E. I. DuPont de Nemours & Co. of Wilmington, Del. Deionized distilled water was used as a temperature calibration material. Temperature was calibrated so that the water peak was at 0° C. About 10 mg of sample material was sealed in an aluminum pan, and scanned from −60° C. to +30° C. at a rate of 5° C./min. An empty pan was used as a reference, and three replicates were performed for each sample. All DSC thermograms were plotted on the same scale to compare the results for each sample with those of deionized distilled water.

Formulations 2, 3, 4 and 5 were prepared as in Example I using the following formulations listed by w/w:

| FORMULATION | 2 | 3 | 4 | 5 |
|---|---|---|---|---|
| INGREDIENT (% w/w) | Flavor #1 Control % | Flavor #2 Control % | Flavor #3 Control % | Flavor #2 Reduced % |
| ENCAPSULATED ACETAMINOPHEN | 35.00 | 35.00 | 42.00 | 42.00 |
| MANNITOL | 30.00 | 30.00 | 22.00 | 22.00 |
| MALTRIN | — | — | 2.00 | 2.00 |
| XANTHAN GUM | 0.30 | 0.30 | 0.30 | 0.30 |
| MAG | 0.30 | 0.30 | 0.30 | 0.30 |
| ASPARTAME | 0.15 | 0.15 | 0.15 | 0.15 |
| FLAVOR #1 | 1.20 | — | 1.20 | — |
| FLAVOR #2 | — | 1.20 | — | 1.20 |
| POLYSORBATE 60 | 0.01 | 0.01 | 0.01 | 0.01 |
| DISTILLED WATER | 33.04 | 33.04 | 32.04 | 32.04 |
| TOTAL | 100.00 | 100.00 | 100.00 | 100.00 |
| g wet mix/ 325 mg tablet | 1.20 | 1.20 | 1.00 | 1.00 |

Figure 5:
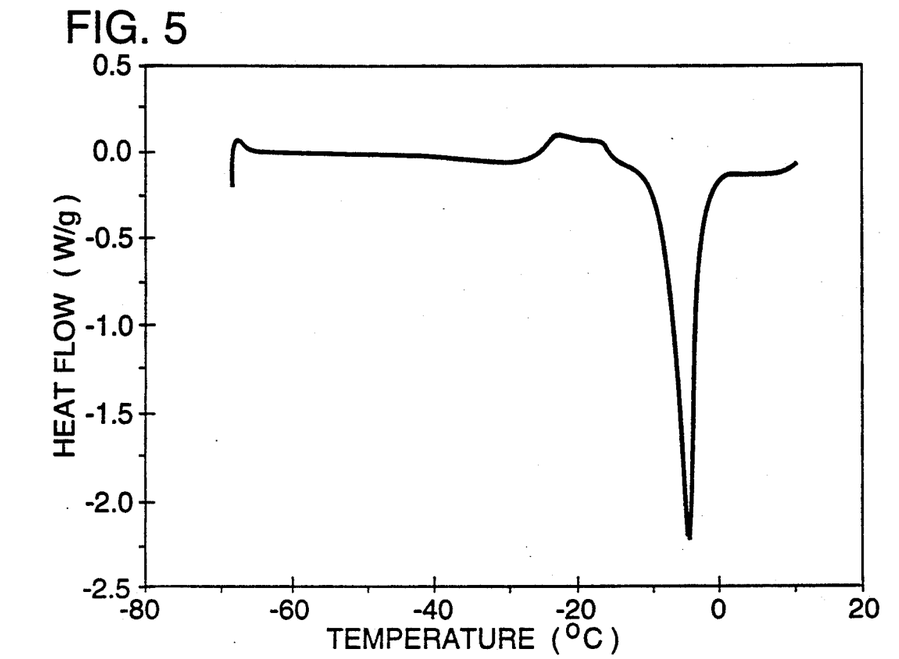
FIGS. 5-7 are differential scanning calorimetry (DSC) thermograms for three of the formulas of the present invention, showing how the collapse temperature of the mixture is determined.
Figure 6:
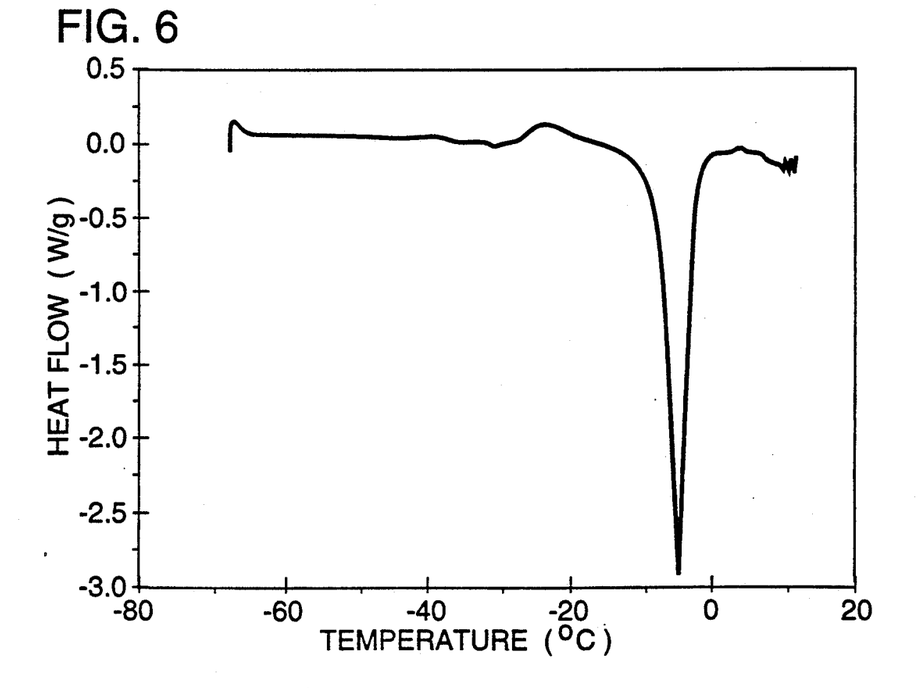
Figure 7:
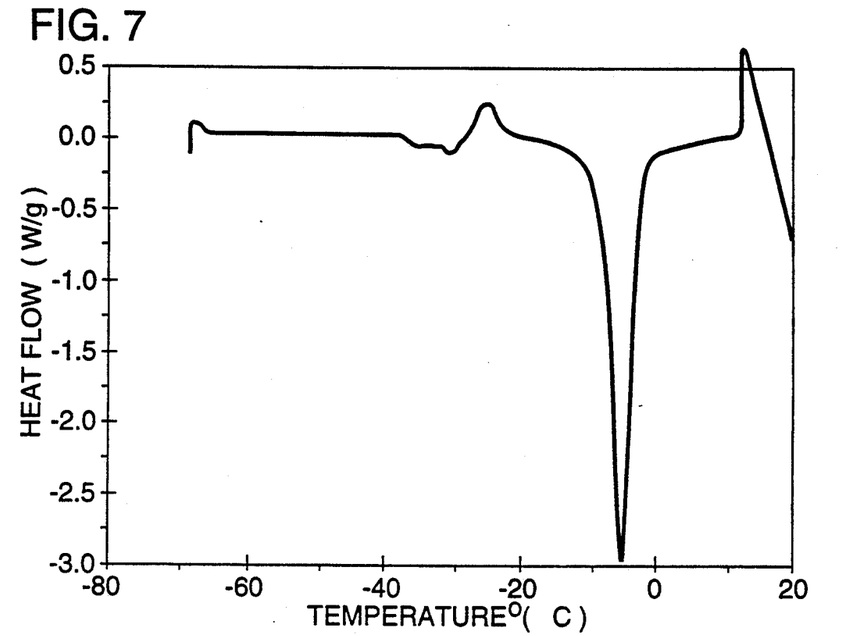

The resulting thermogram for formulation 2 is shown in FIG. 5, while the thermogram for formulation 3 is shown in FIG. 6, and for formulation 4 in FIG. 7. A major endothermic peak occurred in all formulation samples at about −5° C. where solvent ice crystals changed phase from a solid to a liquid This is the equilibrium freezing temperature, which is defined as the temperature at which the mobile solvent (in this case water) is in equilibrium with crystalline solvent One exothermic peak occurred at about −15° C. in formulations 4 and 5, but did not appear in formulations 2 and 3. Another exothermic peak occurred at about −25° C. in all formulations, which was believed to be due to dissolved mannitol changing from a solid to a dissolved solution of mannitol as mannitol particles started to fuse with each other and water molecules in local areas of increasingly mobile water. An exothermic peak is consistent with mannitol's negative heat of solution. Disturbance in the trace between −30° and −40° C. in all formulations was probably due to a glass transition.

The collapse temperature of these formulations was concluded to be about −23° C. because that temperature coincided with the exothermic peak at the lowest temperature. The collapse temperature is the same as the eutectic temperature of a composition. The eutectic temperature is the lowest melting point of a composition, which in the above example is the temperature at which mannitol changes from a crystalline solid state to a liquid solution. The equilibrium freezing point of the composition corresponds to the temperature at which the crystals of the predominant solvent (in this case water) are in equilibrium with the liquid phase. Vacuum drying during the primary drying stage above the collapse temperature allows evaporation of unbound water to occur from a solid through a liquid phase to a gas under controlled conditions. As this phase change progresses, the matrix collapses as crystalline ice becomes more mobile. Maintaining the primary drying temperature below the equilibrium freezing point allows the tablet to be vacuum dried without the explosive disruption that can occur in a vacuum dried product. Removal of moisture from the collapsed matrix leaves behind a dense microstructure that is described in Example VI.

EXAMPLE V

Electrothermal Analysis

Figure 8:
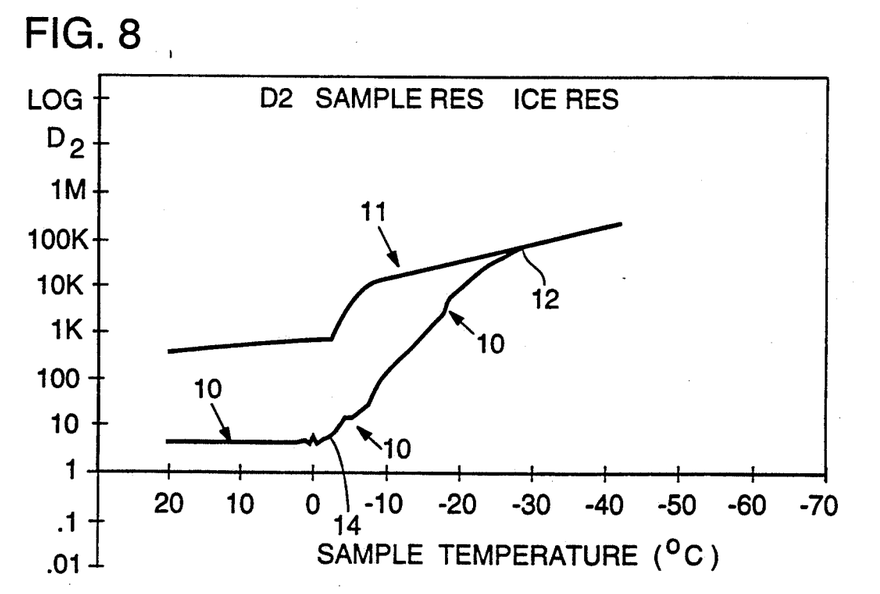
FIG. 8 is a graph of sample temperature versus electrical resistivity showing changes in electrical resistance as the sample reaches its collapse temperature.

The collapse temperature of the matrix can also be determined by electrothermal analysis in which the resistivity of the matrix is measured as a function of temperature. A graph of resistivity (in kilo-ohms) versus sample temperature for one of the tablets of the present invention is shown in FIG. 8. Resistivity for the tablet is shown as line 10, while resistivity of a reference ice sample is shown as line 11 for comparison. The slope of the resistivity plot changes markedly at about −25° C. (illustrated by reference numeral 12 in the drawing), which is the collapse temperature at which the solid becomes more mobile and its resistivity drops. The resistivity of the tablet, which had been substantially the same as the resistivity of ice below −25° C., began to fall more rapidly than the resistivity of ice at temperatures above the collapse temperature. The point of divergence of lines 11 and 12 is at the collapse temperature.

The equilibrium freezing point (reference numeral 14) is also seen to occur at about −5° C. The free water (that is not chemically bound within the matrix) reaches its maximum mobility at this temperature due to its phase change, and resistivity of the matrix becomes substantially constant. Constant resistivity is indicated by line 10 flattening parallel to the temperature axis in FIG. 8. Some bound water remains within the matrix after primary drying, and will be removed during secondary drying above the equilibrium freezing point.

EXAMPLE VI

Electron Photomicrographs

Figure 1:
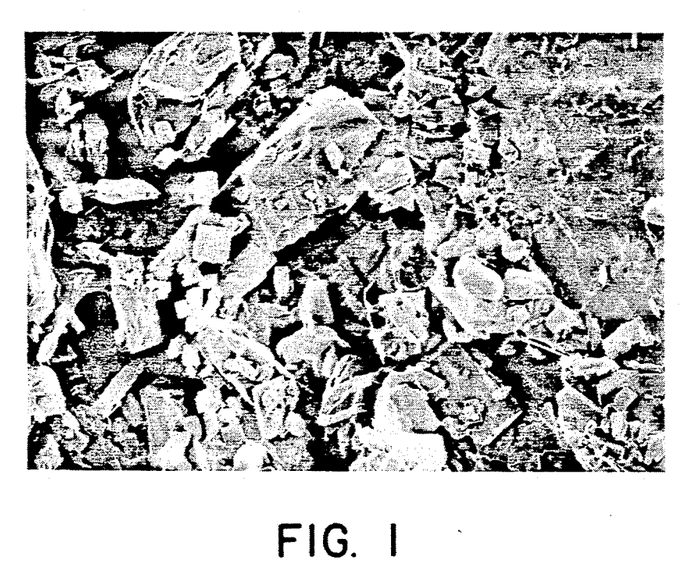
FIG. 1 is a photomicrograph obtained with a scanning electron microscope (SEM) showing the partially collapsed matrix structure of a vacuum dried specimen of the tablet of the present invention at 500× magnification.
Figure 2:
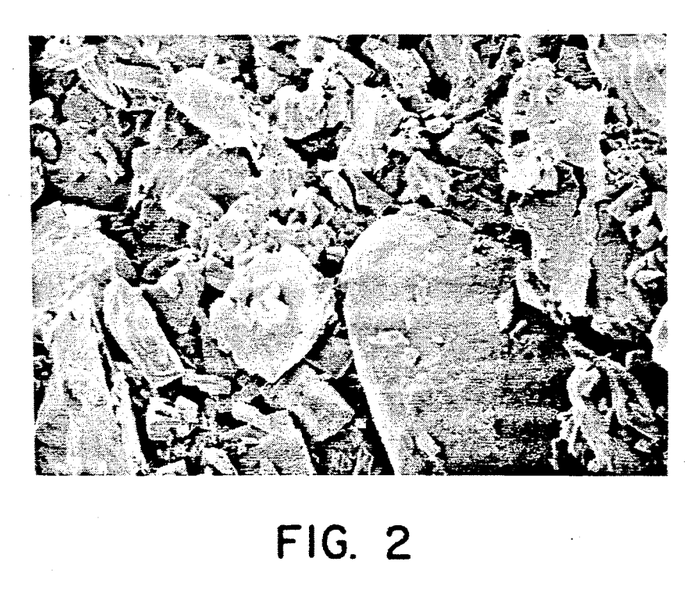
FIG. 2 is another SEM photomicrograph of a vacuum dried specimen at 500× magnification.
Figure 3:
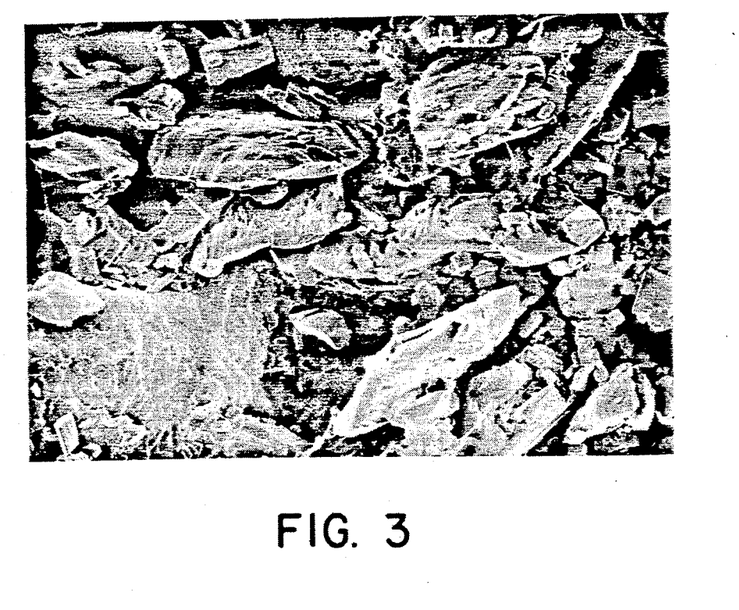
FIG. 3 is a photomicrograph obtained with a scanning electron microscope at 500× magnification showing the open matrix structure of a lyophilized tablet.
Figure 4:
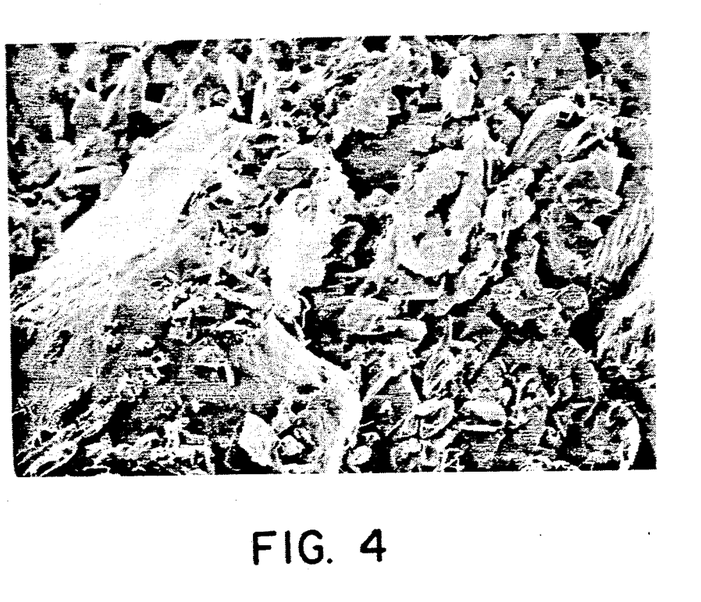
FIG. 4 is another SEM photomicrograph similar to FIG. 3 showing the matrix structure of a lyophilized specimen at 500×, magnification.

To evaluate the physical differences between lyophilized and vacuum dried rapid disintegrating tablets, scanning electron photomicrographs were obtained of both vacuum dried and lyophilized tablet specimens. Vacuum dried specimens are shown in the photomicrographs of FIGS. 1 and 2, while lyophilized specimens are shown in the photomicrographs of FIGS. 3 and 4. An examination of these structures shows that lyophilized specimens in FIGS. 3 and 4 have significantly larger pore diameters and less fused particles than the vacuum dried specimens of the present invention in FIGS. 1 and 2. The overall appearance of the vacuum dried specimens of FIGS. 1 and 2 is much more collapsed and denser than that seen in the lyophilized specimens of FIGS. 3 and 4. The photomicrographs of FIGS. 1 and 2 show a partially collapsed matrix network in the vacuum dried product, as opposed to the open matrix network in the lyophilized product of FIGS. 3 and 4.

The partially collapsed matrix network of the vacuum dried product of the present invention differs from a fully collapsed product, which would be a non-porous solid, such as dust or a solid tablet. Complete collapse of the matrix could be obtained by pressure crushing the tablet. Hence a partially collapsed matrix is at an intermediate point on a continuum from the open matrix lyophilized product to a crushed product having little or no matrix structure. Aside from the physical characteristics of a partially collapsed matrix that are described in this Example and shown in FIGS. 1 and 2, a partially collapsed matrix is alternatively defined to be a matrix produced by vacuum drying the matrix at least partially above the collapse temperature of the matrix, more preferably substantially completely above the collapse temperature, and most preferably completely above the collapse temperature. An example of drying at least partially above the collapse temperature of the matrix is removing about 50% of unbound moisture above the collapse temperature.

EXAMPLE VII

Pharmaceutical and Chemical Ingredients

As used in this specification, a pharmaceutical dosage or delivery form is a tablet, suppository or other solid matrix intended for carrying a substance having therapeutic or diagnostic utility for living subjects, such as humans and animals. The pharmaceutical dosage form of the invention may be employed to administer a wide variety of pharmaceutical substances. Typical drugs that can be administered by means of this invention include, for example, anti-inflammatory agents, such as acetaminophen and ibuprofen; stimulants, such as caffeine; drugs for treating coronary disorders, such as digoxin; oral vaccines; enzymes; peripheral vasodilators and anti-hypertensives, e.g. minoxidil; vasoconstrictors, e.g. ergotamine; analgesics; minor tranquilizers, e.g. lorazepam, oxazepam, diazepam; anti-depressants, e.g.

desipramine; anti-convulsants, e.g. clonazepam; neuromuscular drugs, e.g. pyridostigmine; hormones and oral contraceptives, e.g. ethynyl estradiol and norgestrel; corticosteroids, e.g. prednisolone; local anesthetics; spermicides, e.g. nonoxynol-9; anti-allergics, e.g. diphenhydramine and drugs relieving poisoning and metabolic dysfunction, e.g. methysergide.

The pharmaceutical dosage form is particularly useful for oral administration of drugs. It produces a convenient tablet that can be easily ingested without requiring drinking water. The tablet rapidly disintegrates in the oral cavity of humans and other mammals, making it ideal for administration to uncooperative subjects, such as geriatric, pediatric and verterinary patients. This form of administration can be used to administer drugs which are normally absorbed in the gastrointestinal tract, but is also useful for administration of substances (e.g. nitroglycerin) via the buccal or sublingual route because such drugs may be very rapidly absorbed by the use of the present invention In addition, the matrix of the present invention may be used to add a predetermined amount of chemical to an aqueous medium. For example, the chemical may be a diagnostic compound which is to be added to a biological sample, such as a sample of urine or blood, for determining the amount of a particular constituent present in the sample. Alternatively, it may be desired to add a predetermined amount of chemical reagent to a known amount of aqueous liquid to produce a standardized liquid which can be used, for example, in chemical analysis. The chemical may be a water-soluble or water-dispersible pharmaceutical which can be added to a known amount of aqueous medium to form a pharmaceutical solution or dispersion which can be used for injection or inhalation. Certain chemicals are difficult or hazardous to handle in solution or suspension, and it may be desirable to convert them into a solid form which can be subsequently added to an aqueous medium to produce a solution or dispersion of the chemical In all these instances, the matrix of the present invention disintegrates rapidly and disperses the chemical uniformly throughout the medium.

EXAMPLE VIII

Disintegration Time

The term "rapidly disintegrates" in aqueous solution means that the vacuum dried product disintegrates in less than about 3 minutes when placed in water. The tablet of the present invention preferably disintegrates in more than 10 seconds, more preferably in more than 30 seconds. Especially preferred embodiments disintegrate in one-half to 1 minute. The precise disintegration time is measured by a procedure analogous to the Disintegration Test for Tablets, British Pharmacopoeia 1973. In this procedure, a glass or suitable plastic tube 80 to 100 mm long, with an internal diameter of about 28 mm and an external diameter of 30 to 31 mm, is fitted at the lower end with a basket formed of rustproof wire gauze complying with the requirements for a No. 1.70 sieve. A glass cylinder with a flat base and an internal diameter of about 45 mm contains water not less than 15 cm deep at a temperature between 36° and 38° C.

The basket is suspended centrally in the cylinder and raised and lowered repeatedly in a uniform manner so that at the highest position the gauze just breaks the surface of the water and at the lowest position the upper rim of the basket just remains clear of the water. The tablet is placed in the basket and raised and lowered at a rate that completes the up and down movement thirty times per minute. The article is disintegrated when no particle remains above the gauze that does not readily pass through it.

EXAMPLE IX

Primary and Secondary Drying

The matrix of the present invention is dried during primary drying above the collapse temperature and preferably below the equilibrium freezing point of the matrix. Primary drying refers to the portion of the drying process during which substantially all crystalline unbound moisture is removed from the matrix. Primary drying can be distinguished from secondary drying by observing the temperature of the core of the matrix with a thermocouple. Primary drying ends and only secondary drying occurs when the core temperature of the tablet begins to rise rapidly, as evaporative cooling from primary drying is diminished. This relationship is illustrated in FIG. 9, which plots the progress of the drying process versus the temperature detected at the core of the tablet by a thermocouple.

Figure 9:
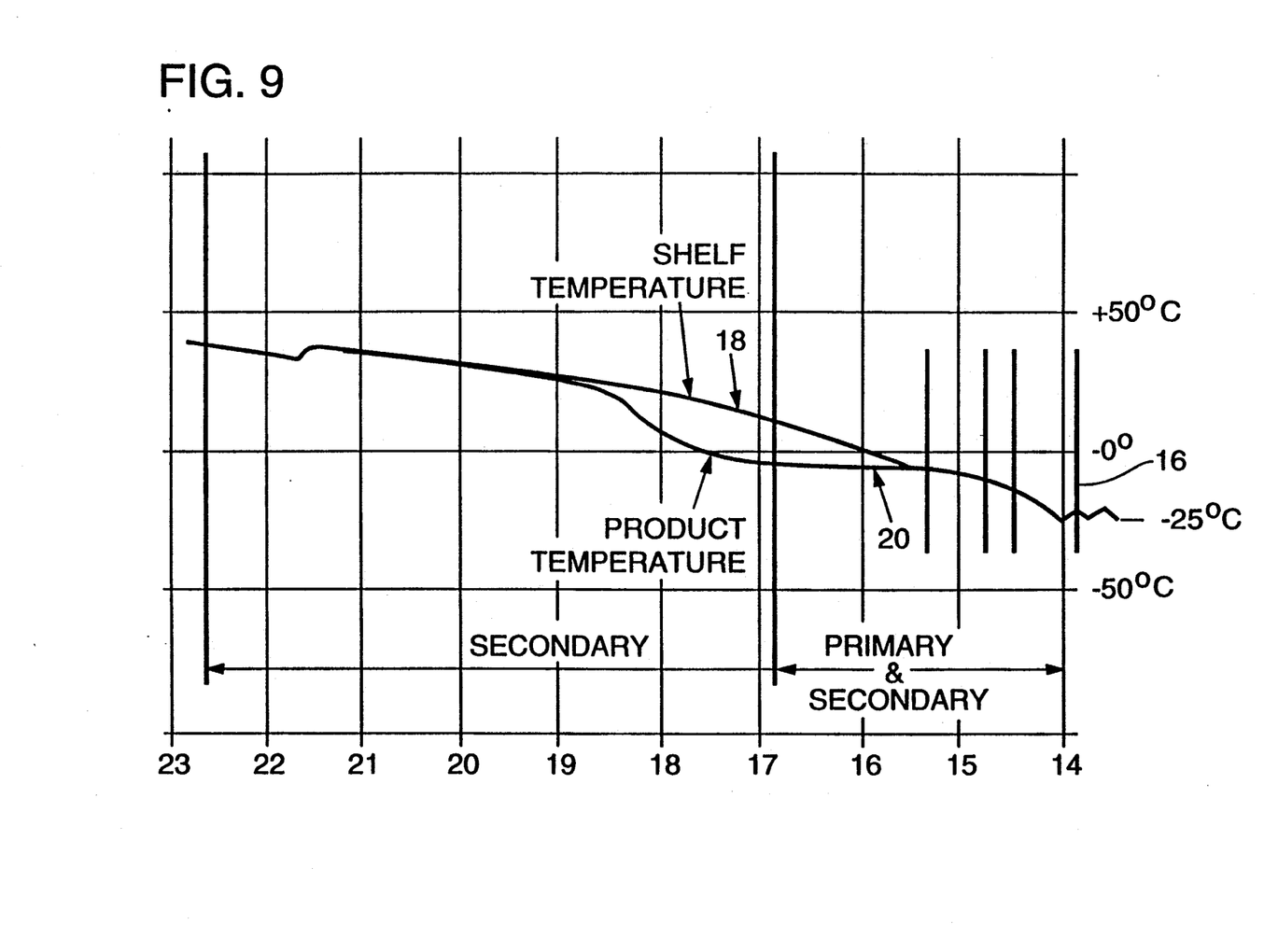
FIG. 9 is a graph showing shelf and tablet temperatures during vacuum drying of a matrix in accordance with the present invention.

A frozen tablet was placed in the vacuum dryer, and the shelf temperature increased to +35° C. at the time indicated by reference numeral 16 in FIG. 9. The shelf temperature increased as shown by line 18, while the tablet temperature increased as shown by line 20. Both primary and secondary drying occurred simultaneously, as described below and shown in the legend on FIG. 9. During the primary drying stage, the temperature of the tablet increased from −25° C. to about the −5° C. equilibrium freezing temperature where removal of the mobilizing solvent occurred. After removal of the unbound water, primarily bound water remained for removal. Bound water (which is always uncrystallized, even at temperatures that freeze the unbound water) is chemically bound within the matrix, for example, by hydrogen bonds. The temperature of the core of the product begins to rise rapidly after primary drying is completed.

As indicated by the legends in FIG. 9, both primary and secondary drying can occur simultaneously. Simultaneous primary and secondary drying occurs because, during the initial stage of vacuum drying, unbound water is removed from the outside of the tablet as a front of primary drying advances inwardly through the matrix. The temperature of the matrix behind the advancing front does not increase significantly because heat is used during primary drying to convert the ice crystals of unbound water from a solid through a liquid phase to a gas. The liquid is then evaporated under the reduced pressure conditions in the dryer. After the unbound water has been removed from behind the advancing front of primary drying, a front of secondary drying begins to advance through the tablet behind the first front. The temperature of the matrix begins to rise because the tablet is no longer cooled by the evaporation of unbound water in areas where secondary drying is now occurring. After the front of primary drying progresses completely inwardly through the core of the tablet, primary drying is complete. The temperature of the tablet rises rapidly as the vacuum drying process enters a stage in which only secondary drying occurs. The difference between primary and secondary drying is seen in FIG. 9 in which the core temperature of the tablet is substantially flat as primary drying occurs, but begins to curve upwardly when primary drying is complete.

As illustrated in the foregoing Example and FIG. 9, primary drying is controlled to occur above the collapse temperature. All, substantially all, or at least a portion of primary drying may occur above the collapse temperature. In especially preferred embodiments, primary drying is controlled to be completed by the time the tablet rises above the equilibrium freezing point of the matrix. It is not essential that all primary drying occur above the collapse temperature. Some sublimation drying may occur, for example, after a frozen tablet is placed in the vacuum dryer. Until the temperature of the tablet rises to the collapse temperature, some removal of bound moisture occurs by sublimation. Alternatively, primary drying may intentionally be performed partially below and partially above the collapse temperature. Such incidental or partial sublimation of unbound moisture is within the scope of this invention, as long as a sufficient amount of moisture is removed by vacuum drying above the collapse temperature to provide a partially collapsed matrix, preferably as shown in FIGS. 1 and 2.

Other examples of the tablet formulations are shown in the following Examples X through XXI.

| Ingredient (gm) | Formulations 6-19 | | | | | | | | | | | | | |
|---|---|---|---|---|---|---|---|---|---|---|---|---|---|---|
| | 6 | 7 | 8 | 9 | 10 | 11 | 12 | 13 | 14 | 15 | 16 | 17 | 18 | 19 |
| ACETAMINOPHEN | 5.00 | 5.00 | 5.00 | 5.00 | 5.00 | 5 | 5 | 5 | 0.25 | 2.5 | 2.5 | 2.5 | 2.5 | 2.5 |
| DEXTROSE | 9.00 | 9.00 | — | 9.00 | — | 8 | 8 | 5.8 | — | 4.3 | 4.3 | 5 | 5 | 4.5 |
| SUGAR | — | — | 9.00 | — | 9.00 | 2 | 2 | 3 | 0.32 | — | — | 2 | 2 | 1.35 |
| XANTHAN GUM | 0.10 | 0.10 | 0.10 | 0.10 | 0.10 | 0.02 | 0.03 | 0.03 | 0.05 | 0.02 | 0.03 | 0.03 | 0.03 | 0.03 |
| POLYSORBATE | 0.02 | 0.02 | 0.02 | — | — | — | 0.02 | 0.05 | 0.05 | 0.02 | 0.02 | 0.02 | — | 0.02 |
| MAG | 0.10 | 0.10 | 0.10 | — | .13(110) | 0.1 | — | 0.1 | 0.03 | 0.09 | 0.1 | 0.1 | 0.15 | 0.1 |
| ACESULFAME K | 0.02 | 0.03 | 0.03 | — | — | — | 0.05 | 0.05 | — | — | — | — | — | — |
| SACCHARIN | — | — | — | 0.90 | 0.54 | — | — | — | — | — | — | — | — | — |
| FLAVOR #1 | — | — | — | 0.30 | — | 0.4 | 0.7 | 0.5 | 0.1 | 0.1 | — | 0.12 | — | — |
| FLAVOR #2 | — | 0.01 | 0.02 | — | — | — | — | — | — | — | — | — | — | — |
| WATER | 35.00 | 16.00 | 16.00 | 14.00 | 14 | 14 | 15.5 | 1.5 | 1.5 | 15 | 10 | 8.35 | 6.3 | 4.5 |
| TOTAL | 49.24 | 30.26 | 30.25 | 28.40 | 28.77 | 29.52 | 29.8 | 31 | | 22.03 | 16.95 | 18.12 | 15.98 | 13 |
| WET ING. | 35.00 | 16.00 | 16.00 | 14.30 | 14.23 | 14.4 | 14.7 | 16 | | 15.1 | 10 | 8.47 | 6.3 | 4.5 |
| DRY ING. | 14.24 | 14.26 | 14.25 | 14.10 | 14.54 | 15.12 | 15.1 | 14 | | 6.93 | 6.95 | 9.65 | 9.68 | 8.5 |
| # TABS | 18 | 18 | 18 | 17 | 17 | 16 | 17 | 17 | | — | | | | |
| WT./TAB | 2.48 | 1.39 | 1.43 | 1.40 | 1.41 | 1.36 | 1.5 | 1.34 | | | | 1.65 | 1.3 | 1.35 |
| MG APAP | 252 | 230 | 235 | 246 | 245 | 230 | 251 | 216 | | 170 | | 229 | 203 | 2.59 |

| INGREDIENT (gm) | Formulations 20-30 | | | | | | | | | | |
|---|---|---|---|---|---|---|---|---|---|---|---|
| | 20 | 21 | 22 | 23 | 24 | 25 | 26 | 27 | 28 | 29 | 30 |
| ACETAMINOPHEN | 5.00 | 5 | 5 | 5 | 5 | 5 | 5 | 5 | 5 | 50 | 5 |
| DEXTROSE | 9.00 | 8.6 | 9 | 9 | 10 | 8 | 8 | 9 | 10 | 100 | 10 |
| XANTHAN GUM | 0.10 | 0.06 | 0.08 | 0.1 | 0.1 | 0.8 | 0.8 | 0.8 | 0.1 | 1 | 0.1 |
| POLYSORBATE | 0.02 | 0.04 | 0.02 | 0.02 | 0.02 | 0.02 | 0.02 | 0.02 | 0.04 | 0.4 | 0.02 |
| MAG | 0.10 | 0.2 | 0.15 | 0.15 | 0.15 | 0.2 | 0.2 | 0.3 | 0.5 | 5 | 0.2 |
| ACESULFAME K | 0.03 | — | — | — | — | — | 0.04 | 0.04 | - | — | 0.01 |
| SACCHARIN | — | — | 1.5 | 2.5 | 2 | 1 | — | — | 1 | 10 | — |
| FLAVOR #1 | 0.01 | — | — | — | — | — | — | — | — | — | — |
| FLAVOR #2 | — | — | 0.1 | 0.15 | 0.15 | 0.12 | — | — | 0.2 | 0.32 | 0.15 |
| FLAVOR #3 | — | — | — | — | — | — | 0.3 | 0.35 | — | — | — |
| WATER | 16.00 | 20 | 16.00 | 15.00 | 12 | 14 | 14 | 20 | 15 | 150 | 12 |
| TOTAL | 30.26 | 33.9 | 31.85 | 31.92 | 29.42 | 28.42 | 27.64 | 34.79 | 31.84 | 316.72 | |
| WET ING. | 16.00 | 20 | 17.50 | 17.50 | 14.00 | 15 | 14 | 20 | 16 | 160 | |
| DRY ING. | 14.26 | 13.9 | 14.35 | 14.42 | 15.42 | 13.42 | 13.64 | 14.79 | 15.84 | 156.72 | |
| # TABS | 18 | | 18 | | 16 | 16 | 13 | | | 30 | |
| WT./TAB | 1.39 | | 1.42 | | 1.39 | 1.47 | 1.66 | | | 1.95 | |
| MG APAP | 230 | | 223 | | 236 | 259 | 300 | | | 308 | |

The most preferred tablets obtained in Example X were those prepared from formulations 6, 7 and 16. The tablets of formulations 18 and 19 were denser than desired. In Example XI, the most preferred tablets were obtained from formulations 20-22, while formulation 24 produced a dense tablet. A high density tablet produces slower dissolution in the mouth.

The acetaminophen (APAP) in Examples X and XI was not encapsulated. In the following Example XII, the acetaminophen was encapsulated. Amounts of gum, polysorbate and sweetener were also varied in this Example, as indicated.

EXAMPLE XII

| | Formulations 31-38 ENCAPSULATED ACETAMINOPHEN (75% APAP; 6.67 G = 5 G APAP AND 1.67 G COTTONSEED OIL) | | | | | | | |
|---|---|---|---|---|---|---|---|---|
| INGREDIENT (gm) | 31 | 32 | 33 | 34 | 35 | 36 | 37 | 38 |
| ENCAPSULATED APAP | 6.67 | 6.67 | 6.67 | 6.67 | 6.67 | 6.67 | 6.67 | 6.67 |
| DEXTROSE | 9.00 | 8.6 | 9.00 | 9.00 | 9.00 | 8.6 | 8.6 | 8.6 |
| XANTHAN GUM | 0.10 | 0.06 | 0.10 | 0.10 | 0.10 | 0.06 | 0.06 | 0.06 |
| POLYSORBATE | 0.02 | 0.04 | 0.02 | 0.02 | 0.02 | 0.04 | 0.04 | 0.04 |
| MAG | 0.1 | 0.2 | 0.1 | 0.1 | 0.1 | 0.2 | 0.2 | 0.2 |

-continued

Formulations 31-38
ENCAPSULATED ACETAMINOPHEN (75% APAP; 6.67 G = 5 G APAP AND 1.67 G COTTONSEED OIL)

| INGREDIENT (gm) | 31 | 32 | 33 | 34 | 35 | 36 | 37 | 38 |
|---|---|---|---|---|---|---|---|---|
| ACESULFAME K | 0.05 | — | 0.03 | 0.03 | 0.03 | — | — | — |
| FLAVOR #1 | 0.01 | — | — | — | — | — | — | — |
| FLAVOR #2 | — | — | 0.15 | 0.15 | 0.15 | 0.15 | 0.15 | 0.15 |
| WATER | 16.00 | 20 | 18.00 | 20.00 | 22.00 | 19 | 18 | 17 |
| TOTAL | 30.26 | 35.57 | 34.07 | 36.07 | 38.07 | 34.72 | 33.72 | 32.72 |
| WET ING. | 16.00 | 20 | 18.00 | 20.00 | 22.00 | 19.00 | 18.00 | 18.00 |
| DRY ING. | 14.26 | 15.57 | 16.07 | 16.07 | 16.07 | 15.72 | 15.72 | 14.72 |
| # TABS | 18 | | | | | | | |
| WT./TAB | 1.39 | | | | | | | |
| MG APAP | 230 | | | | | | | |
| RESULTS | BEST | BEST | | | | | | |

EXAMPLE XIII

Formulations 39-48
Varying Carbohydrate, Flavoring and Sweeteners

| INGREDIENT (gm) | 39 | 40 | 41 | 42 | 43 | 44 | 45 | 46 | 47 | 48 |
|---|---|---|---|---|---|---|---|---|---|---|
| REGULAR APAP OR | 12.5 | — | 12.5 | — | | | | | | |
| ENCAPSULATED APAP | — | 16.68 | — | 3.33 | 3.33 | 3.33 | 3.33 | 16.68 | 16.68 | 16.68 |
| DEXTROSE | 22.50 | 22.5 | 21.5 | | | | 3.67 | | 22.5 | |
| LACTOSE | | | | 3.67 | | | | | | |
| M100 | | | | | | 3.67 | | 15 | | 15 |
| MALTOSE | | | | | 3.67 | | | | | |
| XANTHAN GUM | 0.25 | 0.25 | 0.15 | 0.04 | 0.04 | 0.04 | 0.04 | 0.25 | 0.25 | 0.25 |
| POLYSORBATE | 0.05 | 0.05 | 0.1 | 0.01 | 0.01 | 0.01 | 0.01 | 0.05 | 0.05 | 0.05 |
| MAG | 0.25 | 0.25 | 0.5 | 0.05 | 0.05 | 0.05 | 0.05 | 0.25 | 0.25 | 0.25 |
| SACCHARIN | 2.5 | 2.5 | — | 0.5 | 0.5 | 0.5 | 0.5 | 2.5 | 2.5 | 2.5 |
| FLAVOR | 0.50 | 0.5 | 0.375 | 0.08 | 0.08 | 0.08 | 0.08 | | 0.5 | 0.5 |
| RASPBERRY PUREE | | | | | | | | 10 | | 10 |
| ACETALDEHYDE | | | | | | | | | 0.08 | 0.08 |
| WATER | 40.00 | 40 | 50 | 9 | 9 | 9 | 9 | 35 | 40 | 35 |

The effect of different carbohydrate components was studied in this Example. Lactose and maltose vacuum dries well, but had a less preferred mouth feel than dextrose. M100 is a maltodextrin that also dried well but produced a somewhat chalky mouth feel.

Raspberry puree and acetaldehyde were also used as flavoring agents in this Example.

APAP was encapsulated with cottonseed oil, except for formulation 10 in which APAP was encapsulated with corn oil. Taste masking with corn oil was not found to be as effective as taste masking with cottonseed oil.

Other tablet formations are shown in Examples XV and XVI.

EXAMPLE XV

| INGREDIENT (gm) | Formulations 49-59 | | | | | | | | | | |
|---|---|---|---|---|---|---|---|---|---|---|---|
| | 49 | 50 | 51 | 52 | 53 | 54 | 55 | 56 | 57 | 58 | 59 |
| (ACTUAL APAP) | 12.51 | 15.121% | 12.51 | 19.230 | 22.5 | 26.25 | 15.15 | 30.00 | 29.05 | 29.996 | 22.500 |
| ENCAPSULATED APAP | 16.68 | 20.162% | 16.68 | 25.642 | 30.000 | 35.00 | 20.20 | — | 35.00 | 36.140 | 30.000 |
| DEXTROSE | 22.50 | 27.197% | 22.50 | 24.848 | 20.000 | 20.00 | 27.20 | 20.00 | 20.00 | 20.000 | — |
| MANNITOL | — | — | — | — | — | — | — | — | — | — | 20.000 |
| XANTHAN GUM | 0.25 | 0.302% | 0.25 | 0.311 | 0.300 | 0.30 | 0.30 | 0.30 | 0.30 | 0.300 | 0.300 |
| POLYSORBATE | 0.05 | 0.060% | 0.05 | 0.062 | 0.000 | | 0.06 | 0.10 | 0.10 | 0.100 | 0.000 |
| MAG | 0.25 | 0.302% | 0.25 | 0.311 | 0.300 | 0.30 | 0.30 | 0.30 | 0.30 | 0.500 | 0.300 |
| SACCHARIN | 2.5 | 3.022% | 2.5 | | | | | | | | |
| ASPARTAME | — | — | — | 0.124 | 0.15 | 0.15 | | 0.15 | 0.15 | 0.200 | 0.150 |
| MALTOL | — | — | — | — | — | — | 0.25 | 1.00 | 0.50 | 0.200 | — |
| FLAVOR #1 | 0.50 | 0.604% | — | 0.621 | | | 0.60 | | | | |
| FLAVOR #2 | — | — | 0.025 | | 0.03 | 0.03 | | 0.05 | 0.05 | 0.060 | 0.030 |
| WATER | 40.00 | 48.350% | 40.00 | 48.081 | 49.220 | 44.22 | 51.09 | 48.00 | 43.60 | 44.000 | 49.220 |
| TOTAL | 82.73 | 100.000% | 82.255 | 100.00 | 100.00 | 100.00 | 100.00 | 99.90 | 100.00 | 101.50 | 100.00 |
| WET ING. | 42.50 | | 42.50 | | 49.22 | 44.22 | 51.09 | 48.00 | 43.60 | | |
| DRY ING. | 40.23 | | 39.755 | | 50.78 | 55.78 | 48.91 | 51.90 | 56.40 | | |
| 250 mg wet wt. | 1.65 | | 1.65 | 1.3 | 1.10 | 0.94 | 1.63 | 0.83 | 0.86 | 0.83 | 1.10 |
| 250 mg wet wt. | 0.80 | | 0.80 | | | | | | | | |
| 500 mg wet wt. | 3.30 | | 3.30 | 2.6 | 2.2 | 1.88 | | 1.66 | 1.72 | 1.66 | 2.20 |

| INGREDIENT | Formulation 60 | | | |
|---|---|---|---|---|
| | % | G/250 mg | G/325 mg | g/500 mg |
| DEXTROSE | 27.195% | 0.449 | 0.584 | 0.897 |

-continued

| INGREDIENT | Formulation 60 % | G/250 mg | G/325 mg | g/500 mg |
|---|---|---|---|---|
| ENCAPSULATED APAP | 20.161% | 0.333 | 0.433 | 0.665 |
| FLAVOR #1 | 0.604% | 0.101 | 0.013 | 0.020 |
| XANTHAN GUM | 0.302% | 0.005 | 0.006 | 0.010 |
| MAG | 0.302% | 0.005 | 0.006 | 0.010 |
| CALCIUM SACCHARIN | 0.066% | 0.001 | 0.001 | 0.002 |
| POLYSORBATE | 0.060% | 0.001 | 0.001 | 0.002 |
| WATER | 51.305% | 0.847 | 1.102 | 1.693 |
| TOTAL | 100.000% | 1.650 | 2.148 | 3.300 |

EXAMPLE XVI

| INGREDIENT | Formulation 61 % | G/250 mg | G/325 mg | g/500 mg |
|---|---|---|---|---|
| ENCAPSULATED APAP | 35.000 | 0.333 | 0.434 | 0.665 |
| STALEYDEX | 20.000 | 0.190 | 0.248 | 0.380 |
| XANTHAN | 0.300 | 0.003 | 0.004 | 0.006 |
| MAGNASWEET | 0.300 | 0.003 | 0.004 | 0.006 |
| ASPARTAME | 0.150 | 0.001 | 0.002 | 0.003 |
| FLAVOR | 0.600 | 0.006 | 0.007 | 0.011 |
| WATER | 43.650 | 0.415 | 0.541 | 0.829 |
| TOTAL | 100.000 | 0.950 | 1.240 | 1.900 |

EXAMPLE XVII

In this example, APAP was encapsulated with varying amounts of zein (corn protein soluble in alcohol) as formulations 62-65.

| INGREDIENT (%) | Formulations 62-65 % | .5 ZEIN 62 | .7 ZEIN 63 | 1.0 ZEIN 64 | 1.0 ZEIN 65 |
|---|---|---|---|---|---|
| ACTUAL APAP | 26.25 | 26.25 | 26.25 | 26.25 | 26.25 |
| ENCAPSULATED APAP | 35.00 | 27.63 | 28.23 | 29.17 | 29.17 |
| MANNITOL | 20.00 | 20.00 | 20.00 | 20.00 | 25.00 |
| XANTHAN GUM | 0.30 | 0.30 | 0.30 | 0.30 | 0.30 |
| CORN OIL | — | 0.50 | 0.50 | 0.50 | 0.50 |
| MAG | 0.30 | 0.30 | 0.30 | 0.30 | 0.30 |
| ASPARTAME | 0.15 | 0.15 | 0.15 | 0.15 | 0.15 |
| FLAVOR | 0.60 | 0.60 | 0.60 | 0.60 | 0.60 |
| WATER | 43.65 | 50.52 | 49.92 | 48.98 | 43.98 |
| TOTAL | 100.00 | 100.00 | 100.00 | 100.00 | 100.00 |
| g/250 mg tablet | | 0.95 | 0.95 | | |
| g/325 mg tablet | | 1.24 | 1.24 | | |
| g/500 mg tablet | | 1.91 | 1.90 | | |

EXAMPLE XVIII

Varying levels of mannitol were used in this Example, as shown in formulations 66-69.

| INGREDIENT (%) | Formulations 66-69 | | | |
|---|---|---|---|---|
| | 66 | 67 | 68 | 69 |
| ACTUAL APAP | 27.09 | 27.09 | 27.09 | 27.09 |
| ENCAPSULATED APAP | 35.00 | 35.00 | 35.00 | 35.00 |
| DEXTROSE | 20.00 | — | | |
| MANNITOL | — | 20.00 | 25.00 | 25.00 |
| XANTHAN GUM | 0.30 | 0.30 | 0.30 | 0.30 |
| MAG | 0.30 | 0.30 | 0.30 | 0.30 |
| ASPARTAME | 0.15 | 0.15 | 0.20 | 0.15 |
| FLAVOR | 0.60 | 0.60 | 0.75 | 0.60 |
| WATER | 43.65 | 43.65 | 38.45 | 38.65 |
| TOTAL | 100.00 | 100.00 | 100.00 | 100.00 |
| g/250 mg tablet | 0.92 | 0.92 | | |
| g/325 mg tablet | 1.20 | 1.20 | | |
| g/500 mg tablet | 1.85 | 1.85 | | |

The most preferred tablet density in this Example was obtained with formulation 68 at 25% mannitol.

EXAMPLE XIX

Amounts of mannitol were varied in this Example.

| INGREDIENT (% w/w) | Formulations 70-75 | | | | | |
|---|---|---|---|---|---|---|
| | 70 | 71 | 72 | 73 | 74 | 75 |
| ACTUAL APAP | 27.09 | 27.09 | 27.09 | 27.09 | 27.09 | 27.09 |
| ENCAPSULATED APAP | 35.00 | 35.00 | 35.00 | 35.00 | 35.00 | 35.00 |
| MANNITOL | 30.00 | 15.00 | 20.00 | 25.00 | 20.00 | 20.00 |
| MALTRIN | — | 15.00 | 10.00 | 10.00 | 5.00 | — |
| XANTHAN GUM | 0.30 | 0.30 | 0.30 | 0.30 | 0.30 | 0.30 |

-continued

| INGREDIENT (% w/w) | Formulations 70-75 | | | | | |
|---|---|---|---|---|---|---|
| | 70 | 71 | 72 | 73 | 74 | 75 |
| MAG | 0.30 | 0.30 | 0.30 | 0.30 | 0.30 | 0.30 |
| ASPARTAME | 0.15 | 0.15 | 0.15 | 0.15 | 0.15 | 0.15 |
| FLAVOR | 0.90 | 0.90 | 0.90 | 0.90 | 0.90 | 0.90 |
| POLYSORBATE | 0.01 | 0.01 | 0.01 | 0.01 | 0.01 | 0.01 |
| WATER | 33.34 | 33.34 | 33.34 | 33.34 | 33.34 | 33.34 |
| TOTAL | 100.00 | 100.00 | 100.00 | 100.00 | 100.00 | 100.00 |
| g/250 mg tablet | 0.92 | 0.92 | 0.92 | 0.92 | 0.92 | |
| g/325 mg tablet | 1.20 | 1.20 | 1.20 | 1.20 | 1.20 | |
| g/500 mg tablet | 1.85 | 1.85 | 1.85 | 1.85 | 1.85 | |
| approx dry wts | | | | | | |
| g/325 mg tablet | 0.80 | 0.80 | 0.80 | 0.80 | 0.74 | 0.80 |
| g/500 mg tablet | 1.23 | 1.23 | 1.23 | 1.23 | 1.23 | |

The most preferred tablet in this Example was obtained with the control formulation 70 in which mannitol was present at 30%. This tablet had a good mouth feel, good density, effective taste masking, and good dissolution characteristics.

EXAMPLE XX

| INGREDIENT (% w/w) | Formulations 76-81 | | | | | |
|---|---|---|---|---|---|---|
| | 76 | 77 | 78 | 79 | 80 | 81 |
| ACTUAL APAP | 27.09 | | 27.09 | 27.00 | 27.23 | 27.09 |
| ENCAPSULATED APAP | 35.00 | 70.00 | 35.00 | — | 25.50 | 35.00 |
| MANNITOL | 30.00 | 60.00 | 30.00 | 30.00 | 30.00 | 30.00 |
| XANTHAN GUM | 0.30 | 0.60 | 0.30 | 0.30 | 0.30 | 0.30 |
| CARRAGEENAN | | | | | | 0.30 |
| MAG | 0.30 | 0.60 | 0.30 | 0.30 | 0.30 | 0.30 |
| ASPARTAME | 0.15 | 0.30 | 0.15 | 0.15 | 0.15 | 0.15 |
| FLAVOR | 1.00 | 2.00 | 0.90 | 0.90 | 0.90 | 0.90 |
| ASCORBIC ACID | — | | 0.10 | — | — | 0.30 |
| POLYSORBATE | 0.01 | 0.02 | 0.01 | 0.01 | 0.01 | 0.01 |
| WATER | 33.24 | 66.48 | 33.24 | 41.34 | 40.84 | 33.04 |
| TOTAL | 100.00 | 200.00 | 100.00 | 100.00 | 100.00 | 100.00 |
| g/325 mg tablet | 1.20 | | 1.20 | 1.20 | 1.19 | |
| g/500 mg tablet | 1.85 | | 1.85 | 1.85 | 1.84 | |

Ascorbic acid was added as a flavor enhancer in formulations 78 and 81 of Example XX. Carrageenan was substituted as a gum in formulation 81. Formulation 77 had no encapsulation for APAP, while formulations 78-81 used zein encapsulated APAP.

The foregoing examples illustrate a shaped solid dosage form, such as a tablet, having a partially collapsed matrix containing therein a pharmaceutically active material that is distributed throughout the dosage form. A dosage form is a form (such as a tablet) for administering a dosage of a pharmaceutically active material. A pharmaceutically active material is a material that has a hysiological or biological effect on an organism to which it is administered, and in particularly preferred embodiments is a therapeutic substance used to treat a pathological condition. The material is distributed throughout the dosage form or tablet as particles carried within the matrix. The material is preferably distributed substantially uniformly throughout the matrix, i.e. in substantially equal dosages per unit matrix. It is also possible to provide a concentrated dose in one region of the matrix.

Vacuum drying is preferably performed substantially completely below the equilibrium freezing point of the matrix, which means at least about 80% of the bound moisture, preferably 90%, most preferably about 100%, is removed from the matrix during primary drying below the equilibrium freezing point.

The present invention, in some very specific embodiments, also includes a method of dispensing tablets of the present invention from a blister pack by forcing them through a foil back on a blister pack. The invention also includes methods of administering the tablets to a subject (such as a human or animal) by placing the tablet in the oral cavity of the subject.

Having illustrated and described the principles of the invention in several embodiments, it should be apparent to those skilled in the art that the invention can be modified in arrangement and detail without departing from such principles. We claim all modifications coming within the spirit and scope of the following claims.

We claim:

1. A method of preparing a shaped pharmaceutical dosage form for oral administration as a solid that rapidly disintegrates in an aqueous solution, the method comprising the steps of:
   preparing a mixture comprising sufficient amounts of a pharmaceutical compound, a gum, a carbohydrate base, and a solvent to form a partially collapsed matrix network when the mixture is frozen and vacuum dried to remove the solvent above a collapse temperature of the matrix for a sufficient period of time to form the matrix;
   shaping the mixture into a desired pharmaceutical dosage form shape;
   freezing the mixture; and
   vacuum drying the frozen mixture above the collapse temperature of the mixture for a sufficient period of time to form the partially collapsed matrix network.

2. The method of claim 1 wherein the mixture is vacuum dried substantially completely above the collapse temperature.

3. The method of claim 1 wherein the gum is selected from the group consisting of acacia, guar, xanthan, tragacanth gum, and mixtures thereof, and the carbohydrate is selected from the group consisting of mannitol, dextrose, sucrose, lactose, maltose, maltodextrin, corn syrup solids, and mixtures thereof.

4. The method of claim 2 wherein the vacuum drying step further comprises vacuum drying the mixture substantially completely below an equilibrium freezing point of the mixture.

5. The method of claim 1 wherein the mixture has a collapse temperature of about −23° C.

6. The method of claim 3 wherein the mixture comprises (w/w) about 20–30% mannitol and 0.01–0.3% xanthan gum.

7. A method of preparing a shaped tablet for oral administration as a solid that rapidly disintegrates in an aqueous solution, the method comprising the steps of:
preparing a mixture comprising a pharmaceutically active material, a solvent, and a pharmaceutical carrier containing a gum and a carbohydrate that forms a partially collapsed matrix network with the pharmaceutically active material distributed throughout the matrix when the mixture is frozen and vacuum dried above the collapse temperature of the matrix;
shaping the mixture into the form of a tablet and freezing the mixture; and
vacuum drying the mixture substantially completely above a collapse temperature of the mixture and substantially completely below an equilibrium freezing point of the mixture to form the partially collapsed matrix network.

8. The method of claim 1 further comprising the step of retarding a phase change that occurs at a collapse point by vacuum drying below about 0.5 torr when a reaction temperature is within about 5° C. above the collapse temperature of the matrix.

9. The method of claim 8 further comprising the step of vacuum drying above about 2.0 torr as the matrix temperature approaches the equilibrium freezing point.

* * * * *